(12) United States Patent
Zwislocki et al.

(10) Patent No.: US 9,295,585 B1
(45) Date of Patent: Mar. 29, 2016

(54) EAR MUFFLER

(71) Applicant: Syracuse University, Syracuse, NY (US)

(72) Inventors: Jozef J. Zwislocki, Fayetteville, NY (US); Gregory D. Post, Fairport, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 14/483,447

(22) Filed: Sep. 11, 2014

(51) Int. Cl.
*A61F 11/06* (2006.01)
*A61F 11/14* (2006.01)

(52) U.S. Cl.
CPC ...................... *A61F 11/14* (2013.01)

(58) Field of Classification Search
CPC ......... A61F 11/12; A61F 11/06; A61F 11/08; A61F 2011/085; H04R 2460/09
USPC ................................................. 181/129, 135
See application file for complete search history.

(56) References Cited

U.S. PATENT DOCUMENTS

| | | |
|---|---|---|
| 2,454,731 A | 3/1951 | French |
| 3,565,069 A | 2/1971 | Miller |
| 4,441,576 A | 4/1984 | Allen |
| 4,807,612 A | 2/1989 | Carlson |
| 4,852,683 A | 8/1989 | Killion |
| 5,113,967 A | 5/1992 | Killion et al. |
| 5,781,272 A | 7/1998 | Bright et al. |
| 5,824,967 A | 10/1998 | Zwislocki |
| 6,484,842 B1 | 11/2002 | Widmer et al. |
| 7,489,794 B2 * | 2/2009 | Harvey .......................... 381/380 |
| D596,286 S | 7/2009 | Post et al. |
| 7,697,706 B2 | 4/2010 | Doty |
| 7,740,104 B1 | 6/2010 | Parkins et al. |
| 7,882,928 B2 | 2/2011 | McMahon et al. |
| 8,107,638 B2 | 1/2012 | Zwislocki |
| 8,161,974 B2 | 4/2012 | Post et al. |
| RE43,595 E | 8/2012 | Lederer |
| 2006/0162992 A1 * | 7/2006 | Seville .......................... 181/135 |
| 2008/0152177 A1 | 6/2008 | Watanuki et al. |
| 2014/0016808 A1 * | 1/2014 | Cherukuri et al. ............ 381/324 |

* cited by examiner

*Primary Examiner* — Jeremy Luks
(74) *Attorney, Agent, or Firm* — Barclay Damon, LLP (57) ABSTRACT

A passive semi-insert noise reducing device configured for insertion into the ear of a subject includes at least one muffler tube having a closed end and an opposing open end, the muffler tube being configured to be secured to the head of a subject. The at least one muffler tube is defined by an elongate hollow tubular section, including the closed end, and a transverse hollow tube at the open end that is configured for placement in the outer ear of the subject. The at least one muffler tube is defined by a length that produces quarter wave resonance in low audible sound frequencies. A soft sealing member disposed onto an exterior surface of the hollow connecting tube has a distal end surface that is substantially flush with the open end of the muffler tube.

30 Claims, 5 Drawing Sheets

EAR MUFFLER

TECHNICAL FIELD

This application is generally directed to the field of noise reducing devices and more specifically to a passive semi-insert noise reducing device configured for insertion into the outer ear of a subject.

BACKGROUND

Conventional prior art devices that are configured to protect or defend the ear against excessive noise can be divided into three (3) major classes; namely, ear plugs, ear muffs and semi-inserts. There are a number of differences between each of these device classes. More specifically, ear plugs are inserted into the ear canal while ear muffs cover the entire outer ear and are held in place by appropriate support means, such as a head band. Semi-inserts are held against the entrance of the ear canal by means similar to those used for ear muffs. Each class of device also has its own advantages and disadvantages.

In this regard, ear plugs can provide substantial noise reduction (attenuation) distributed reasonably evenly over the audible frequency range of sound. In addition, these devices are small and inexpensive. However, ear plugs may cause discomfort due to their required positioning in the ear canal. These devices may also cause hygiene problems resulting from cerumen (ear wax) and the possibility of introducing harmful substances into the sensitive ear canal that may produce irritation as well as infection of the ear canal walls. Further, there is the added problem of fitting ear plugs to individual ear canals, which vary in size and shape over a fairly wide range.

Ear muffs may provide the highest noise attenuation at sound frequencies exceeding 1000 Hz, but these latter devices are generally inferior to ear plugs at lower frequencies. Although these frequencies appear to be less damaging for the ear, they produce relatively strong masking of useful signals, such as speech, and can have a fatiguing effect. Because of their size, conventional ear muffs are cumbersome and can become uncomfortable when worn for prolonged periods of time. That is, these devices further exert pressure on the sides of the head when worn and additionally can produce a bothersome warming effect to the wearer. Additionally, ear muffs are significantly more expensive than either ear plugs or semi-insert devices.

Semi-inserts reduce the problems of individual fit and hygiene found in ear plugs and are less cumbersome and less expensive than ear muffs. Several prior art versions of these devices however have provided less noise attenuation. In an effort to improve the effectiveness of semi-insert devices in terms of noise (attenuation) reduction, Applicants have previously developed a passive semi-insert ear defending device, as described in U.S. Pat. No. 5,824,967, and referred to herein as an "ear muffler".

Figure 1:
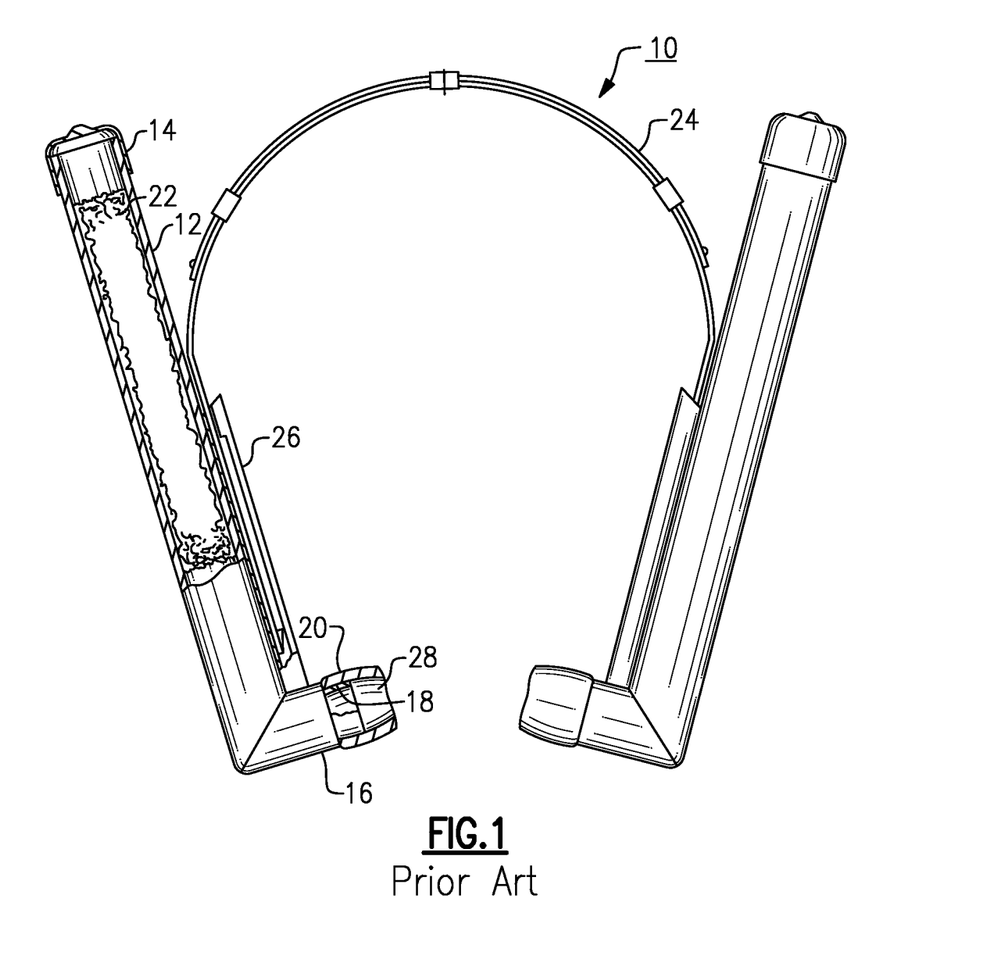
FIG. 1 is a front partially sectioned view of a passive ear noise reducing device made in accordance with the prior art.

As shown in FIG. 1 and described in the '967 patent, an exemplary ear muffler 10 comprises a cylindrical hollow muffler tube 12 closed at one end using a cap 14 and connected to the ear canal (not shown) through an extension 16 and connecting tube 18 of a reduced diameter that enables an adequate fit with the outer ear. The end of the connecting tube 18 defines an opening 28 to provide communication with the ear canal. A tight fit of the connecting tube 18 with the ear canal is achieved by means of a soft foam sealing cuff 20, which is fastened to the connecting tube 18. The muffler tube 12 is filled with a sound absorbing material 22 such as cotton, felt or nylon fibers, and is held in place on the head of the wearer (not shown) by means of a springy headband 24, the headband 24 being adjustably mounted on the tube 12 with the help of a holder 26, the latter being firmly attached to the muffler tube 12. To achieve a tight seal around the ear canal entrance, the springy headband 24 is made to gently press the connecting tube 18 against the ear, so as to provide a compressive force for the connecting tube 18 and more specifically the soft sealing cuff 20 protruding beyond the connecting tube 18. Only one half of the ear muffler 10 is shown in detail in FIG. 1, with the remaining half being a mirror image and also having a muffler tube, extension and connecting tube, each configured to be disposed symmetrically on the other side of the head of the wearer.

In terms of the operation of the device 10, the noise reduction (sound attenuation) that is achieved can be described by the relation $P_a/P_e = A_s = (Z_e + Z_s)/Z_e$, in which $P_e$ is the sound pressure at the entrance of the ear canal, $P_a$ is the sound pressure in ambient air, $A_s$ is the sound attenuation, $Z_e$ is the acoustic impedance at the entrance of the ear canal and $Z_s$ is the acoustic impedance of the seal provided by the semi-insert through which sound must penetrate into the ear canal. If $Z_s$ is much larger than $Z_e$, as it should be in effective devices, the above formula can be approximated by $A_s = Z_s/Z_e$ showing that the sound (noise) attenuation is directly proportional to the acoustic impedance at the entrance of the ear canal. Using a muffler tube, such as that described according to FIG. 1, the noise attenuation is increased by placing a small acoustic impedance $Z_m$, in parallel with the impedance of the ear canal $Z_e$. When $Z_m$ is sufficiently small, the sound attenuation approaches $A_{sm} = Z_s/Z_m$ and the improvement in sound attenuation becomes $A_m/A_s = (Z_e/Z_m)$. In the limit, the improvement in sound attenuation is proportional to the ratio between the ear canal and the shunting impedances.

The muffler tube 12 together with its hollow extension 16 measures about 13 cm in length and provides a quarter wave resonance around 650 Hz, which further increases the ambient noise reduction in the broad vicinity of this frequency. Additional details relating to this sound defending device are provided in the '967 patent, referenced above, the entire contents of which are herein incorporated by reference.

Though the passive semi-insert device described by the '967 patent is a significant improvement over other previously known semi insert devices, it has been later determined that further improvements can be made. For example, the soft sealing cuff extends significantly outward from the end of the connecting tube and is prone to vibrations and also can create a potential source of noise leakage. In addition, there are additional features that can be added to further tune or suitably adjust damping characteristics of the device.

BRIEF DESCRIPTION

Therefore and according to one aspect, there is herein described a passive semi-insert device configured for insertion into the ear of a subject and reducing the effect of ambient noise. The device comprises at least one muffler tube having a closed end and an opposing open end, in which the at least one muffler tube is configured to be secured to the head of a subject. The at least one muffler tube comprises an elongate hollow tubular section including the closed end, and a hollow tube extension and a connecting tube at the open end, each substantially transverse to the tubular section, the connecting tube being configured for placement in the outer ear of the subject and wherein the at least one muffler tube is defined by a length that provides quarter wave resonance in low audible sound frequencies. A sealing member is disposed onto an exterior surface of the connecting tube such that a distal end surface of the sealing member is substantially flush with the open end of the muffler tube.

The sealing member is preferably made from a visco-elastic material and is configured to provide a seal with the outer ear of the wearer. As noted, the sealing member is attached to the exterior of the connecting tube. According to one version, the connecting tube can include at least one annular exterior feature, such as a retaining ring, onto which the sealing member can be attached. In another version, a distal portion of the connecting tube can be shaped, such as by tapering, to insure an interference fit with the sealing member.

According to at least one version, the at least one muffler tube is provided with at least one damping feature that is suitably configured for broadening and reducing acoustic resonance of the passive semi-insert device.

In at least one embodiment, the damping feature can include a quantity of sound-absorbing material disposed in at least one axial portion of the muffler tube. This sound-absorbing material, which can include cotton, nylon or other synthetic fibers is wholly disposed within the volume of the muffler tube over the axial portion(s) thereof.

In another embodiment, the damping feature comprises at least one thin rigid plate having a single slit formed therein, the plate being transversely disposed in relation to the primary axis of the tube. The at least one rigid plate is defined by an outer diameter that is sized to engage an inner diameter of the muffler tube. In at least one embodiment more than one rigid slitted plate can be disposed within the muffler tube, thereby creating adjacent chambers, each plate acting as an acoustic resistor. According to yet another version, the at least one damping feature comprises at least one wire bundle that is disposed within at least an axial portion of the muffler tube. The wires in the bundle extend in a direction that is parallel to the axis of the tubular portion in which the outer diameter of the wire bundle is sized to engage the inner diameter of the tubular portion so as to substantially fill the interior of the muffler tube. The relative spacing between wires, as well as the individual wire diameters in the bundle, can be appropriately sized in order to control the degree of damping.

In another version, the noise reducing device can include an earphone and/or a microphone, for example, enabling attachment to a smartphone, a tablet computer, an Mp3 player or other electronic device. According to one embodiment, the earphone or microphone can extend outwardly from the closed end of the muffler tube. In another version, the earphone or microphone can be separately attached to the device.

In at least one version, the noise reducing device can be designed such that the hollow tube extension and connecting tube are built as a single component, along with the tubular section of the muffler tube.

In one version, the hollow tube extension and connecting tube can be defined by a substantially circular cross section. In another version, the tube extension and connecting tube can be defined by a substantially oval cross section.

According to another aspect, there is provided a method for manufacturing a passive semi-insert noise reducing device. The method comprises providing at least one muffler tube defined by a closed end and an opposing open end, the at least one muffler tube further comprising an elongate hollow tubular section, a transverse hollow tube extension and a connecting tube, the latter being adapted to be fitted within the ear of a subject. A sealing member is provided over the connecting tube such that a distal end surface of the sealing member is substantially flush with the open end of the muffler tube.

According to at least one version, at least one damping feature comprises a quantity of sound absorbing material disposed within at least and axial portion of the muffler tube. In another version, a damping feature comprises at least one thin rigid plate transversely disposed within the muffler tube, the at least one rigid plate having an outer diameter sized to engage an inner diameter of the tubular section and having a single slit to act as an acoustic resistor. According to at least one embodiment, at least two thin rigid plates can be transversely disposed in separate axial sections of the muffler tube.

In another version, the at least one damping feature comprises at least one tightly packed bundle of wires disposed within at least an axial portion of the muffler tube, said at least tightly packed bundle having an outer diameter that is sized to engage an inner diameter of the muffler tube, the at least one wire bundle being disposed in a direction substantially coaxial with a major dimension of the muffler tube. In at least one embodiment, the method further comprises disposing at least two tightly packed wire bundles in separate axial sections of the muffler tube.

According to at least one version, the method further comprises attaching the sealing member onto at least one retaining ring on an exterior surface of the connecting tube. A portion of the hollow tube extension, including the connecting tube, can be defined by a substantially oval cross section. At least a portion of the connecting tube can include a tapered or otherwise shaped surface to provide an interference fit with the sealing member for retaining same. Preferably, the sealing member is at least partially made from a visco-elastic material.

One advantage provided by the herein described passive semi-insert device and method is improved noise attenuation over previously known ear defending devices, including previously known muffler tubes.

Yet another advantage realized is that comfort is surprisingly increased by having the sealing member with its end surface substantially flush with the end of the connecting tube of the herein described noise reducing device.

Still another advantage is that the herein described noise reducing device can be easily manufactured and is cost efficient in terms of labor and affordability to the user.

These and other features and advantages will be readily apparent from the following Detailed Description, which should be read in conjunction with the accompanying drawings.

BRIEF DESCRIPTION OF THE DRAWINGS

FIG. 4(*a*) is a front facing view of the passive semi-insert noise reducing device of FIG. 2 in a partially assembled configuration;

FIG. 4(*b*) is an enlarged view of a portion of the semi-insert noise reducing device of FIG. 4(*a*) and more specifically the hollow tube extension thereof;

DETAILED DESCRIPTION

The following description relates to a number of exemplary embodiments of a passive semi-insert noise reducing device configured to be worn on the head of a user. Throughout this discussion, several terms are used in order to provide a suitable frame of reference in regard to the accompanying drawings. These terms such as "top", "bottom", "distal", "proximal", "over", "under", "interior", "exterior" and the like should not be interpreted in a manner that reduces the effective scope of the herein described device and method for use and manufacture. In addition, the drawings are merely intended to convey the salient features of the device and related method and are not necessarily drawn to scale. To that end, the reader should not overly rely upon any scaling or dimensions that are presented in the drawings.

Figure 2:
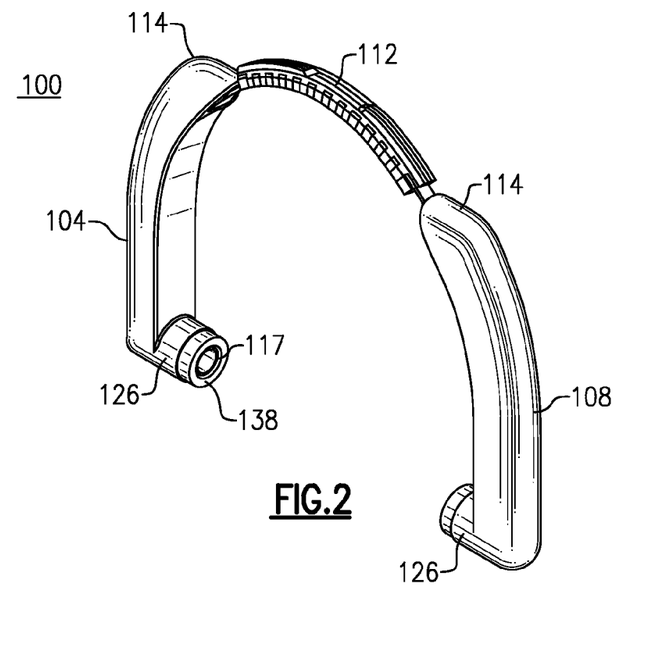
FIG. 2 is a perspective view of a passive semi-insert noise reducing device in accordance with a first exemplary embodiment.
Figure 3:
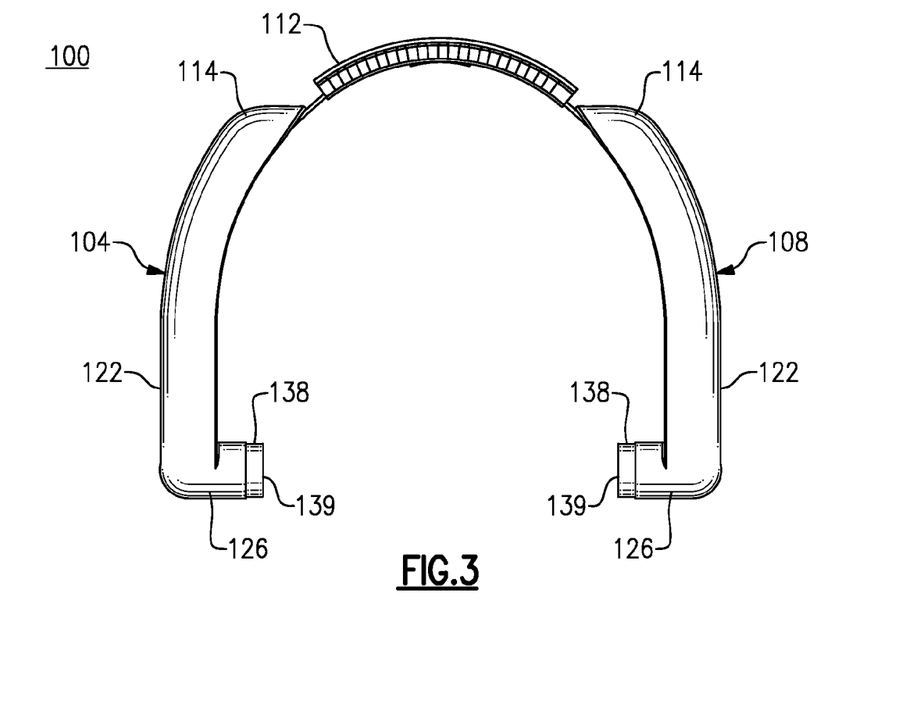
FIG. 3 is a front facing view of the passive semi-insert noise reducing device of FIG. 2.

Referring to FIGS. 2 and 3, there is shown perspective and front facing views, respectively, of a passive semi-insert noise reducing device 100 made in accordance with a first exemplary embodiment. The passive semi-insert device 100 includes a pair of muffler tubes 104, 108 that are interconnected by means of a springy elastic band 112 that is configured to engage the head of the wearer, the elasticity of the band 112 being sufficient to provide a retaining force that must be overcome in order to remove the device 100. In at least one version, the elastic band 112 is preferably adjustable to accommodate the head of the wearer. As shown herein, the muffler tubes 104, 108 are each defined by a shape that substantially conforms with the head of a wearer (not shown). According to this embodiment, each muffler tube 104, 108 is manufactured from a lightweight durable plastic material, such as ABS (acrylonitrile butadiene styrene), and further defined by a closed end 114. Alternatively, each muffler tube 104, 108 including the closed end 114 could include a separate cap or other closure means (not shown). Each muffler tube 104, 108 further is defined by an open end 117 as well as a hollow interior. More specifically, each muffler tube 104, 108 includes an elongate tubular portion 122 and a transverse hollow tube extension 126, the latter extending to a connecting tube 130, FIG. 4, having a smaller diameter than that of the hollow tube extension 126 which terminates at the open end 117. As noted, the muffler tubes according to this exemplary embodiment are shaped to more closely conform with the head of a wearer. More specifically, the upper end of each tubular portion 122 is angled inwardly relative to the remainder of the portion. The connecting tube 130, FIG. 5, is sized to be fitted within the outer ear of the wearer along with a sealing member 138 that overlays the exterior of the connecting tube 130. Preferably, the sealing member 138 is made from a visco-elastic material in order to provide a comfortable interface between the device 100 and the wearer and also to provide a suitable seal with the ear canal.

The sealing member 138 according to this specific embodiment is defined by a circular hollow cross section in which a distal end surface 139 of the sealing member 138 is substantially flush with the open end 117 of the muffler tube 104 when attached; that is, the distal end surface 139 of the sealing member 138 is coplanar with a distal end of the connecting tube 130. It has been surprisingly determined that the additional overhanging length found in prior sealing cuffs for muffler tubes provides an additional source of protection loss. It has further been found that the foregoing design is more surprisingly more comfortable than prior designs having sealing cuffs that protrude outwardly (axially) from the end of the connecting tube.

Figure 4A:
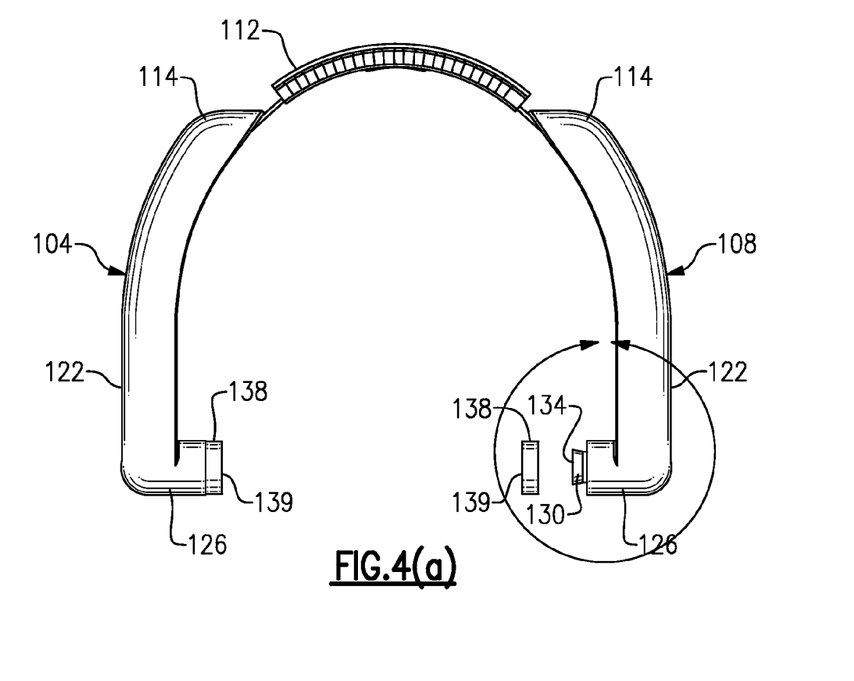
Figure 4B:
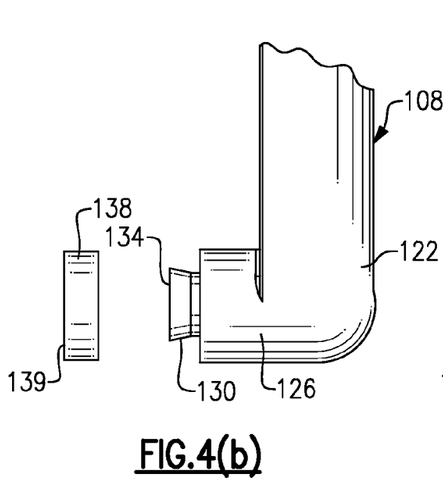
Figure 5:
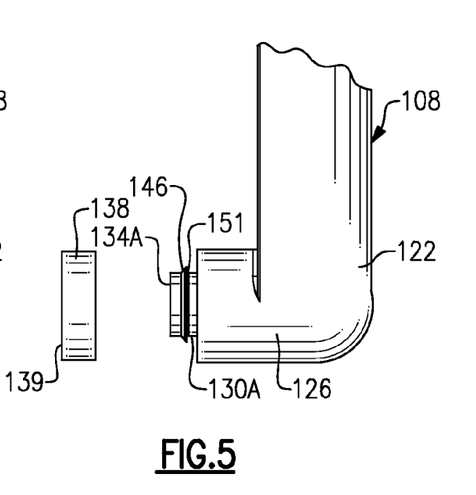
FIG. 5 is an enlarged view of an alternative hollow tube extension for the semi-insert noise reducing device and in accordance with yet another exemplary embodiment.

Referring to FIGS. 4(a) and 4(b), the herein described noise reducing device 100 is shown in a partially assembled mode with the sealing member 138 removed from the connecting tube 130. In this version, the connecting tube 130 is formed with a tapered configuration in which the outer diameter of the connecting tube 130 is largest at its distal end and in which the sealing member 138 can be pulled onto the connecting tube 130 to effectively retain same using an interference fit. An alternative construction is depicted in FIG. 5 in which the connecting tube 130A includes an exterior retaining ring 146 having at least one circumferential ridge 151 onto which the sealing member 138 can be attached. Still further, the sealing member 138 could be secured to the connecting tube 130 using other suitable attachment means.

The hollow tube extension 126, including the connecting tube 130, 103A according to these exemplary embodiments has a substantially circular cross section. However, the tube extension 126 can alternatively have an oval or other suitable cross-section without sacrificing overall functionality.

As previously discussed, the theory of operation of the herein described device and more specifically noise reduction (sound attenuation) is provided by the formula $P_a/P_e = A_s = (Z_e + Z_s)/Z_e$, in which $P_e$ is the sound pressure at the entrance of the ear canal, $P_a$ is the sound pressure in the ambient air, $A_s$ is the sound attenuation, $Z_e$ is the acoustic impedance at the entrance of the ear canal and $Z_s$ is acoustic impedance of the seal provided by the semi insert through which sound must penetrate into the ear canal. If $Z_s$ is much larger than $Z_e$, as it should be in effective devices, the above formula can be approximated as $A_s = Z_s/Z_e$, showing that the sound (noise) attenuation is directly proportional to the acoustic impedance of the seal and inversely proportional to the acoustic impedance at the entrance of the ear canal. In the herein described muffler tubes 204, 208, the noise attenuation is increased by placing a relatively small acoustic impedance $Z_m$, in parallel with the impedance of the ear canal, $Z_e$. When $Z_m$ is sufficiently small, the sound attenuation approaches $A_{sm} = Z_s/Z_m$.

The tubular section 122 and the connecting tube 126 are each hollow and combine to define an acoustic chamber of the muffler tube 104, 108, this chamber having an overall length that produces quarter wave resonance over a small range of audible frequencies. According to this exemplary embodiment, the length of the hollow tube extension 126 is about 9 mm, the diameter of the connecting tube 130 is about 13 mm, the thickness of the connecting tube 130 is about 1.3 mm and the length of the tubular section 122 is about 136 mm in which the overall length of each muffler tube 104, 108, including the tubular portion 122 and hollow tube extension 126, is about 145 mm. It will be understood that these components can assume other suitable dimensions wherein the specifically noted dimensions are merely exemplary.

As previously discussed, each of the muffler tubes 104, 108 can be manufactured from a hard durable plastic, such as ABS (acrylonitrile butadiene styrene), wherein each of the components of the herein described device 100 can be produced using a molding process for ease of manufacture. It will be readily apparent, however, that other suitable structural materials could alternatively be utilized.

Figure 6:
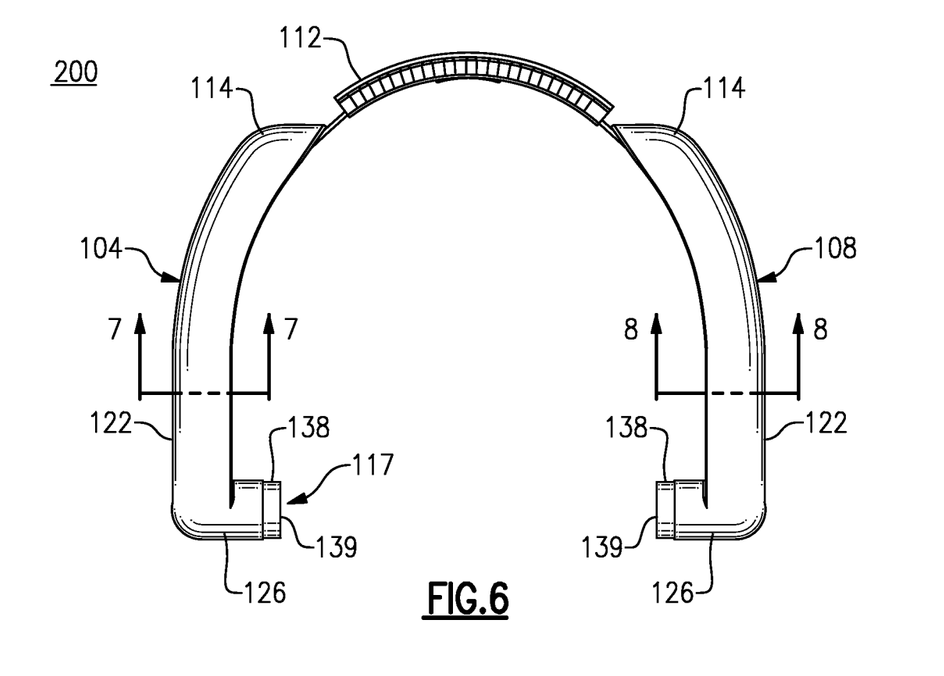
FIG. 6 is a front facing view of a passive semi-insert noise reducing device in accordance with yet another exemplary embodiment.
Figure 7:
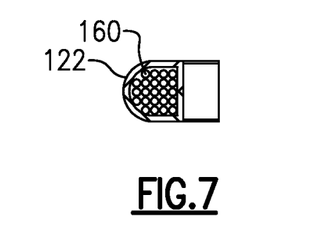
FIG. 7 is a partial sectioned view of a portion of a passive semi-insert noise reducing device taken through lines 7-7 of FIG. 6 in accordance with still another exemplary embodiment and relating to a damping feature.
Figure 8:
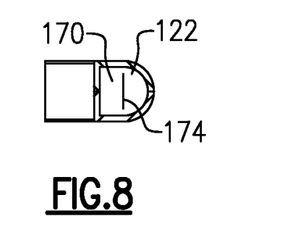
FIG. 8 is a sectioned view of a portion of a passive semi-insert noise reducing device taken through lines 8-8 of FIG. 6 and relating to an alternative damping feature.

In addition and referring to FIGS. 6-8, at least one damping feature can be provided within the elongate tubular section 122 of the ear muffler. Two separate exemplary embodiments are depicted herein for purposes of a single semi-insert device 200. It will be readily understood, however, that this discussion based on the single device is for better effecting the description of features.

First and referring to FIG. 6, the device 200 is similar to that previously described herein. Similar parts are herein labeled with the same reference numerals for the sake of clarity. More specifically, the passive semi-insert device 200 includes a pair of muffler tubes 104, 108 that are interconnected by means of a springy elastic band 112 that is configured to engage the head of the wearer, the elasticity of the band 112 being sufficient to provide a retaining force that must be overcome in order to remove the device 100. The band 112 is preferably adjustable to accommodate the head of the wearer. As shown herein, the muffler tubes 104, 108 are each defined by a shape that more closely conforms with the head of a wearer (not shown). According to this embodiment, each muffler tube 104, 108 is preferably manufactured from a lightweight durable plastic material and defined by a closed end 114. Alternatively, each muffler tube 104, 108 including the closed end 114 could include a separate cap or other closure means (not shown). Each muffler tube 104, 108 further is defined by an open end 117 and a hollow interior.

More specifically, each muffler tube 104, 108 of this device 200 also includes an elongate tubular portion 122 and a transverse hollow tube extension 126, the latter extending to a connecting tube 130A, FIG. 5, having a smaller diameter than that of the hollow tube extension 126 which terminates at the open end 117 and having a retaining ring 146, FIG. 5. The connecting tube 130A is sized to be fitted within the outer ear of the wearer and includes a sealing member 138 that overlays the exterior of the short connecting tube 126 and more specifically the retaining ring 146. Preferably, the sealing member 138 is made from a visco-elastic material in order to provide a comfortable interface between the device 100 and the wearer and also to provide a suitable seal with the ear canal.

As in the preceding and according to this exemplary embodiment, the sealing member 138 is defined by a circular hollow cross section in which a distal end surface 139 of the sealing member 138 is substantially flush with the open end 117 of the muffler tube 104 when attached; that is, the distal end surface 139 of the sealing member 138 is coplanar with a distal end of the connecting tube 130.

Referring to FIGS. 6 and 7 and according to an exemplary embodiment, the hollow interior of at least one of the muffler tubes 104 can be configured with a damping feature defined by at least one tightly packed bundle of wires 160. The wire bundle 160 is configured to extend in a direction that is parallel or coaxial to the major (length) dimension of the tubular section 122. The properties (diameter, thickness) of the wires can be suitably adjusted, as well as the relative spacing between the wires in the bundle 160 to control damping. According to one embodiment, a single bundle of wires 160 can be provided in each tubular section 122. Alternatively, a plurality of tightly packed wire bundles 160 can be positioned in various axial portions of each muffler tube 104, 108, in which each bundle 160 substantially fills the cross-section thereof.

Referring to FIGS. 6 and 8, and in lieu of the wire bundle(s), a thin rigid plate 170 can be transversely disposed within the interior of the hollow tubular section 122, the plate 170 having a single slit 174 formed preferably at the center thereof, enabling use as an acoustic resistor. According to this exemplary embodiment, the thickness of the thin rigid and transversely disposed plate 170 is about 0.0021 inches and the slit 174 is approximately 0.0005 inches in width.

According to at least one embodiment, a plurality of thin rigid slitted plates (not shown) can be provided, each slitted plate 170 being appropriately spaced from each other within the tubular section 122 in order to define adjacent chambers within the semi-insert device 200 that are configured to control damping.

According to yet another embodiment, a quantity of sound-absorbing material, which can include cotton, nylon or other synthetic fibers is wholly disposed within the volume of the muffler tube and over an axial portion(s) thereof.

At least one or combinations of the above described damping features can be provided in order to achieve a suitable damping effect. Other similar features could be substituted.

Figure 9:
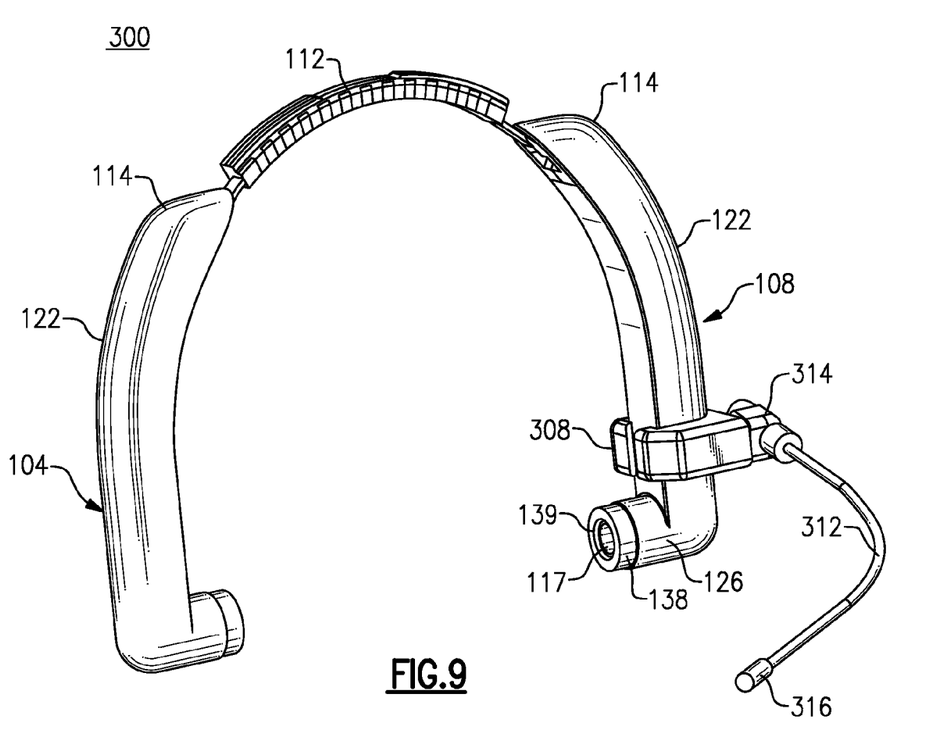
FIG. 9 is a perspective view of a passive semi-insert noise reducing device made in accordance with yet another exemplary embodiment.

In addition, an earphone or a microphone can be included with the herein described device. In one exemplary version as shown in FIG. 9, a microphone can be directly connected to one of the elongate sections 122 via a support 308 which retains an adjustable arm 312 through an attachment structure 314 and in which the microphone 316 is disposed at an extending (unsupported) end of the adjustable arm 312. In another version, an earphone or microphone can be wirelessly connected to the device, such as using a transmitter and antenna disposed within the device through an IR, RF or other suitable connection.

PARTS LIST FOR FIGS. 1-9

10 ear muffler
12 hollow cylindrical muffler tube
14 cap
16 extension
18 connecting tube
20 sealing cuff
22 sound absorbing material
24 head band
26 holder
28 opening
100 device, passive semi-insert
104 muffler tube
108 muffler tube
112 band, elastic
114 closed end
117 open end
122 elongate tubular section
126 hollow tube extension
130 connecting tube
130A connecting tube
134 distal surface, connecting tube
138 sealing member
139 distal end surface, sealing member
146 exterior retaining ring
151 circumferential ridge
160 wire bundle
170 plate, thin rigid
174 slit
200 device, passive semi-insert
300 device, passive semi-insert
308 support
312 adjustable arm
314 attachment structure
316 microphone It will be readily apparent from the preceding discussion that other modifications and variations are possible based on the concepts discussed herein, and in accordance with the following claims.

The invention claimed is:

1. A passive semi-insert device that engages against the ear canal, for reducing the effect of ambient noise, the semi-insert device comprising:
   at least one muffler tube having a closed end and an opposite open end, the at least one muffler tube being configured to be secured to the head of a subject and comprising:
      an elongate hollow tubular section including the closed end;
      a transverse hollow tube extension at the open end which is configured to engage against the ear canal of the subject, the at least one muffler tube being defined by a length that provides quarter wave resonance in low audible sound frequencies; and
   a sealing member disposed onto an exterior surface of the transverse hollow tube extension, the sealing member having a distal end surface that is substantially flush with the open end of the muffler tube in order to create a seal against the ear canal and in which the sealing member is held against the ear canal using a head band that provides a compressive force.

2. The device as recited in claim 1, further comprising at least one damping feature for broadening and reducing the acoustic resonance of the device.

3. The device as recited in claim 2, wherein the at least one damping feature comprises a quantity of sound-absorbing material filling the interior of at least an axial portion of the interior of the muffler tube.

4. The device as recited in claim 2, wherein the at least one damping feature comprises at least one thin rigid plate disposed in the muffler tube, the at least one thin rigid plate being transversely disposed in relation to a primary axis of the tubular portion and sized to engage an inner diameter of the tubular portion, the at least one thin rigid plate having a narrow slit configured to act as an acoustic resistor.

5. The device as recited in claim 4, including at least two of the thin rigid plates separately and axially disposed within the muffler tube, each of the thin rigid plates having narrow slits defined therein and in which the thin rigid plates divide the muffler tube into adjacent chambers.

6. The device as recited in claim 2, wherein the at least one damping feature comprises at least one tightly packed wire bundle disposed in at least a portion of the muffler tube, the at least one wire bundle extending in a direction that is coaxial with a major dimension of the elongate tubular section, the at least one wire bundle having an outer diameter that engages an inner diameter of the tubular section.

7. The device as recited in claim 6, wherein at least two of the wire bundles are disposed in separate axial sections of the muffler tube.

8. The device as recited in claim 1, wherein the sealing member is at least partially made from a visco-elastic material.

9. The device as recited in claim 1, wherein the transverse hollow tube extension comprises at least one retaining ring disposed on an exterior surface of the hollow tube extension and in which the sealing member is attached upon the at least one retaining ring.

10. The device as recited in claim 1, wherein at least a portion of the hollow tube extension includes a tapered surface configured to retain the sealing member.

11. The device as recited in claim 1, wherein at least a portion of the transverse hollow tube extension is defined by a substantially oval cross section.

12. The device as recited in claim 1, wherein at least a portion of the transverse hollow tube extension is defined by a substantially circular cross section.

13. The device as recited in claim 1, wherein the transverse hollow tube extension is defined by a first portion having a first diameter and an adjacent second portion having a second diameter which is smaller than the first diameter and wherein the sealing member is retained on the second portion.

14. The device as recited in claim 1, in which the muffler tube is formed with a transverse end portion having the same diameter as the remainder of the tubular section, wherein the transverse hollow tube extension extends from the transverse end portion and is defined by a diameter that is smaller than the diameter of the tubular section.

15. The device as recited in claim 1, comprising two muffler tubes connected by an elastic band to permit securement of the device to the head of a subject.

16. The device as recited in claim 1, further comprising a microphone.

17. The device as recited in claim 16, wherein the microphone is wireless.

18. The device as recited in claim 1, further comprising an earphone.

19. The device as recited in claim 1, wherein the hollow transverse tube extension includes a tapered surface configured to provide an interference fit with the sealing member.

20. A method for manufacturing a semi-insert passive noise reducing device, the method comprising:
   providing at least one muffler tube defined by a closed end and an opposing open end, the at least one muffler tube further comprising an elongate hollow tubular section and a transverse hollow tube; and
   attaching a sealing member over the exterior of the transverse hollow tube such that an extending end surface of the sealing member is substantially flush with the open end of the muffler tube, wherein the distal end of the transverse hollow tube and end surface of the sealing member engage against the ear canal of a subject in order to provide an effective acoustic seal, the seal being maintained using a head band in order to provide a compressive force to maintain the acoustic seal.

21. The method as recited in claim 20, further providing at least one damping feature in the at least one muffler tube.

22. The method as recited in claim 21, wherein the at least one damping feature comprises a quantity of sound absorbing material disposed within a portion of the muffler tube.

23. The method as recited in claim 21, wherein the at least one damping feature comprises at least one thin rigid plate disposed within the muffler tube, the at least one thin rigid plate having an outer diameter sized to engage an inner diameter of the tubular section and having a single slit to act as an acoustic resistor.

24. The method as recited in claim 23, further comprising disposing at least two of the thin rigid plates in separate axial sections of the muffler tube, each of the thin rigid plates having single narrow slits defined therein.

25. The method as recited in claim 21, wherein the at least one damping feature comprises at least one tightly packed bundle of wires disposed within at least an axial portion of the muffler tube, the at least tightly packed bundle having an outer diameter that is sized to engage an inner diameter of the muffler tube, the at least one wire bundle being disposed in a direction coaxial with a major dimension of the muffler tube and forming interstices between the disposed wires of the at least one bundle that create acoustic resistance.

26. The method as recited in claim 25, wherein the method further comprises disposing at least two tightly packed wire bundles in separate axial sections of the muffler tube.

27. The method as recited in claim 25, wherein the sealing member is attached onto at least one retaining ring formed on an exterior surface of the transverse hollow tube.

28. The method as recited in claim 20, wherein the method further comprises defining at least a portion of the hollow connecting tube by a substantially oval cross section.

29. The method as recited in claim 20, wherein the hollow section comprises a first portion and an axially adjacent second portion wherein the sealing ring is formed on the exterior of the second portion.

30. The method as recited in claim 20, wherein a portion of each muffler tube is transverse and is defined by the same diameter as the remainder of the muffler tube and the transverse hollow tube extends axially from the transverse portion and is defined by a smaller diameter.

\* \* \* \* \*